(12) United States Patent
Kerr

(10) Patent No.: US 8,936,564 B2
(45) Date of Patent: Jan. 20, 2015

(54) BIO-COMPATIBLE CATHETER

(76) Inventor: Marshall Kerr, Carlsbad, CA (US)

( * ) Notice: Subject to any disclaimer, the term of this patent is extended or adjusted under 35 U.S.C. 154(b) by 0 days.

(21) Appl. No.: 13/422,973

(22) Filed: Mar. 16, 2012

(65) Prior Publication Data
US 2013/0053755 A1    Feb. 28, 2013

Related U.S. Application Data

(60) Provisional application No. 61/528,060, filed on Aug. 26, 2011.

(51) Int. Cl.
| | |
|---|---|
| *A61M 37/00* | (2006.01) |
| *A61M 5/00* | (2006.01) |
| *A61M 25/00* | (2006.01) |
| *A61M 1/28* | (2006.01) |
| *A61L 29/10* | (2006.01) |
| *A61L 29/14* | (2006.01) |
| *A61M 1/10* | (2006.01) |

(52) U.S. Cl.
CPC ............. *A61M 1/285* (2013.01); *A61L 29/106* (2013.01); *A61L 29/14* (2013.01); *A61M 25/0045* (2013.01); *A61M 1/1008* (2013.01); *A61L 2400/10* (2013.01)
USPC ............................ 604/6.16; 604/8; 604/93.01

(58) Field of Classification Search
CPC ............ A61F 9/00781; A61M 27/006; A61M 27/008; A61L 31/16; A61L 31/10; C23C 14/28
USPC ......... 604/6.16, 8, 264, 266, 523, 93.01, 104, 604/540; 427/2.1, 2.24, 2.25, 2.28, 2.3, 427/561, 566, 569, 476
See application file for complete search history.

(56) References Cited

U.S. PATENT DOCUMENTS

| | | | | |
|---|---|---|---|---|
| 4,054,139 | A * | 10/1977 | Crossley | 604/265 |
| 5,468,562 | A * | 11/1995 | Farivar et al. | 428/457 |
| 5,770,255 | A * | 6/1998 | Burrell et al. | 427/2.1 |
| 2003/0050691 | A1* | 3/2003 | Shifrin et al. | 623/1.23 |

OTHER PUBLICATIONS

N. Ozkucur, C. Wetzel, F. Hollstein, E. Richter, R. H. W. Funk and T. K. Monsees, "Physical vapor deposition of zirconium or titanium thin films on flexible polyurethane support adhesion and physiology of human endothelial cells", Apr. 10, 2008, Wiley InterScience, Journal of Biomedical Research Part A, vol. 89A Issue 1, p. 60.*
Donald M. Mattox, "Handbook of Physical Vapor Deposition (PVD) Processing",1998, William Andrew Inc., p. 649.*

* cited by examiner

*Primary Examiner* — Melanie Hand
*Assistant Examiner* — Ned T Heffner
(74) *Attorney, Agent, or Firm* — Donn K. Harms

(57) ABSTRACT

A bio-compatible lumen bearing device such as a catheter formed of a polymeric material having a titanium surface bonded to the underlying exposed catheter surface. The titanium surface is employed in patients to improve bio-compatibility and enhance lubricity during insertion and removal.

7 Claims, 2 Drawing Sheets

BIO-COMPATIBLE CATHETER

This application claims priority to Provisional Application No. 61/528,060 filed on Aug. 26, 2011, and is incorporated herein by reference in its entirety.

BACKGROUND OF THE INVENTION

1. Field of the Invention

The present invention relates generally to catheter devices which are inserted into a body cavity, duct, or vessel of a human or animal patient to allow drainage, administration of fluids or gases, or access by surgical instruments. More particularly, it relates to catheters which are inserted and positioned in patients for longer time frames such as periphery inserted central catheters (PICC or PICC line) and to a PICC line which enhances bio compatibility through a titanium exterior surface.

2. Prior Art

Catheters have been employed in medicine since the late 19th century and disposable catheters have been used widely since the mid 20th century. Modern disposable catheters are constructed from a range of polymeric materials including polyethylene, polyurethene, silicone rubber, latex, and thermoplastic elastomers. Silicone is one of the most common choices because it is considered substantially inert and unreactive to body fluids and a range of medical fluids with which a catheter may come into contact.

Conventionally, modern disposable catheters are made from polyurethane and are provided by manufacturers in different lengths and sizes for men, women, children and animals. The most advanced catheters have a thin surface coating (hydrophilic coating). When immersed in water or a water bearing fluid, this hydrophilic coating swells to a smooth, slippery film making the catheter safer and more comfortable to insert.

PICC lines are an intravenous form of a catheter used in the medical field. Such PICC lines are often left implanted in a patient for consecutive uses for prolonged periods of medical treatment. Examples of a long term venous engagement of PICC lines includes chemotherapy and extended antibiotic therapy, to name a few.

In use, generally speaking, the PICC line is inserted in a peripheral vein, most commonly in the upper arm of the patient, and extends to the terminating end near large blood vessels in the chest of the patient, proximate to their heart. Such positioning of the distal end of the catheter provides a long term intravenous access for placing medicine in the blood stream near the heart. The catheter, being typically a slender flexible tube generally also employs a guide wire to aid in inserting and positioning the distal end of the catheter in the patient's body and is commonly known in the art.

After such insertion, the catheter employed as a PICC line is conventionally left engaged in the blood vessels of the patient for periods of weeks or months. While engaged with patient in this as-used position, when not in use, the PICC line can be flushed out and capped off. When medicine is to be communicated to the patient's bloodstream, communication is provided through the axial passage of the PICC line exiting at the distal end near the heart.

Because PICC lines and other forms of catheters remain in an engagement with a patient's body, potentially for long time periods, cleanliness and bio-compatibility of the engaged catheter are highly important and infection can be a continuing problem for a patient. When bio-compatibility is an issue, the patient's vein may become infected or irritated by the line, often referred to as mechanical phlebitis. Further, fibrin or other encapsulate may adhere to the catheter causing further complications.

Bio-compatibility of catheters is often dictated by the catheter material or coating thereof. Current conventional catheters employ silicone, polyvinyl chloride, or latex rubber tubing which may have an exterior with a silver, hydrogel, or silicone coating. However, these materials incur some problems with breakage, waste disposal after use, blood clot formation, infection, and allergy concerns.

As such there exists an unmet need for an improved catheter with enhanced bio-compatibility for employment where such a catheter is anticipated to be engaged with a patient for long time periods of weeks or months. Additionally, such a catheter having such improved bio-compatibility would be a benefit for patients who are especially sensitive to catheter insertion even for short periods of time.

Such an improvement should be easily employed with existing catheter designs and the installed base of such medical catheters to allow for easy and widespread distribution to help patients immediately. Such an improvement should also be employable at a reasonable cost to thereby allow for low-cost bio-compatible catheters to thereby ensure widespread distribution and use and to thereby provide improved medical services to the largest number of patients.

SUMMARY OF THE INVENTION

The device and method herein disclosed and described provides a solution to the shortcomings in catheter prior art and achieves the above noted goals through the provision of an easily employed bio-compatible surface for catheter exteriors. By positioning a thin layer of titanium on the exterior circumferential surface of polyurethane and other catheters, the device and method herein provide a means to render conventional catheters into catheters with increased bio-compatibility. Such increased bio-compatibility may additionally be accomplished by providing a layer of titanium on the interior surface and end walls of the catheter in combination with the above noted exterior surface layer. To that end the device herein will aid patients by providing a means for increased biological tolerance to a long term insertion of the device in their artery, vein, or other body cavity or organ.

It is particularly preferred that bio-compatible material is titanium which is coated, sprayed, thermoformed, film-engaged, or otherwise engaged to the exterior of conventional catheters using any other engagement means as would occur to those skilled in the art of catheter construction and/or engaging a bio-compatible surface to catheters and the like. However, titanium being lubricious as well as providing other properties discussed below, is preferred.

Titanium modernly has been found in most humans to generally elicit little to no immune system response. Additionally, as a general rule it lacks any toxic or other injurious effect on the patient's body. Consequently, it is frequently employed for implants as it can be left in the body for extended periods of time without discomfort, infection, or irritation. As such, titanium has replaced stainless steel for long term oral implants, and many joint and bone implants where strength is a requirement and long term body acceptance is a must. Such titanium implants are generally formed in a manner to take advantage of the material's light weight but great strength and resistance to bending and deterioration.

The device and method herein, provides the bio-compatibility of titanium in a different manner than that of generally thick and strong titanium implants which are made not to yield to force and to support weight. Rather than forming solid implants for a long term which are unyielding and permanently mounted, the device formed by the method herein, positions titanium, in a very thin and flexible covering, upon the entire surface of the circumference of the exterior surface of a conventional catheter formed of for instance polyethylene or of a silicone elastomer. Still in other modes, increased bio-compatibility, lubricity, and anti-pathogenic qualities can be achieved by additionally coating the interior surface and ends of the catheter as well.

The titanium surface may be adhered in a number of processes, such as using titanium films which are electron-beam evaporated onto the exterior of the catheter using a chemical vapor deposition (CVD), which is a process for the metallization of complex components while at the same time achieving strong bonds directly with the material of the underlying device substantially into a unitary structure of titaniumized polymeric material. However, as this process involves temperatures in excess of 150° C., it is not an option for many prosthetic and polymeric materials which would not be shape retentive at such temperatures (e.g. polypropylene). For that reason, the titaniumization of polymeric material forming the catheter takes place at low temperatures using a special plasma-coating process known as PACVD (plasma-activated chemical vapor deposition). Plasma is the term used for an excited (ionized) gas. In that stage, atoms/molecules are highly energetic. However, plasma is not hot such as the plasma in fluorescent tubes.

In the titaniumization process to coat the catheter surfaces herein with titanium, gaseous titanium is introduced into a coating chamber as a precursor. By adding energy in the form of plasma, the precursor is split into individual ionized atoms. These ionized titanium atoms have free electrons at their surfaces. In addition to the precursor, the plasma also excites the surfaces of the polymeric material of the catheter, with the result that their surfaces also have free electrons. The ionized titanium atoms come into contact with the ionized surface of the implant resulting in the formation of covalent bonds and the titanium is thus almost permanently bonded to the plastic. The process is performed at temperatures less than 120 degrees centigrade preserving the extruded polymeric material shape, structure, and flexibility.

This process creates a composite polymeric and titanium material whose surface is coated with an ultra-thin, approx. 20-60 nm (1 nanometer=1 millionth of a millimeter), highly bio-compatible layer of titanium. The coating in this range is important to render the coating thin such that it appears to be transparent. Further, maintaining the bonding of the titanium in the range noted, provides a means to maintain the lumen bearing device highly flexible since the bonded coating is also. While thicker bonded surfaces may be employed, it would begin to over metallize the surfaces and render them less flexible which is undesirable in a lumen bearing device such as a catheter which must negotiate sharp body passage turns and twists. Consequently, maintaining the process temperature below that of the polymeric material, and maintaining the bonded coating in the range of 20-60 nm, provides a means to maintain the original flexibility of the polymeric material forming the lumen bearing structure.

Because the titanium precursor is introduced in gaseous form, it may be communicated to contact all parts of the polymeric lumen device such as a catheter. Using a pump or fan to induce airflow into the gas and communicate it through the axial passage of the catheter during the process, the interior wall surface and the end wall surfaces may also be bonded with the titanium. As a result, the entire interior and outer surfaces, including gaps in between complex shapes, may be completely and evenly titaniumized.

In a similar process, the titanium may be bonded to a film surface where the titanium is in a film and thereafter the combined film is thermoformed to the exterior of the polyethylene or silicone or other material forming the exterior of the catheter. It is envisioned that those skilled in the art will endeavor to employ other means of bonding titanium to one or all surfaces of a catheter in other manners and methods and such are anticipated such as employing a titanium mixture and carrier adhesive which may be coated to the exterior surfaced of the material forming the catheter. Further, the material forming the catheter wall defining the lumen or lumens, may be impregnated with titanium oxide to yield a solid solution of polymeric material and titanium dioxide which is extruded to yield a catheter with surfaces all having titanium communicating with the body tissues of a patent in which it is inserted.

Of course those skilled in the art will ascertain there are a number of ways to adhere a titanium surface or layer to the exterior of the material forming catheter be it a short term catheter or longer term employed PICC line type catheter, and any such manner as would occur to one skilled in the art for adhering a titanium exterior layer to such a catheter is anticipated within the scope of this application.

An additional benefit of the invention herein is that it need not be removed should the patient require an MRI. Since titanium is non-ferromagnetic, even prolonged exposure to an MRI procedure would have little effect on the device, and the non-ferrous titanium makes very little disturbance in the magnetic field of the MRI which would inhibit imaging.

Adhered in such a thin layer, the exterior surfacing of titanium which contacts the body tissues, does little to effect the flexibility of the catheter as is needed to advance the catheter through the patient's vein or artery. Titanium has better flexibility qualities than most metals and in the very thin layer of this invention, this ductile quality allows for good flexibility. Further utility is found in that titanium has anti-thrombogenic qualities, meaning that in addition to the fact that the titanium surfaced catheter is bio-compatible during long term exposure in the patient, blood clots also do not easily form, and is further desirous in that manner. Additionally, it has been found that the titanium surface increases lubricity and is anti-pathogenic.

It is particularly preferred that the methods of positioning the titanium on the exterior surface of the catheter is to bond the titanium to the polymeric material forming the catheter at the covalent level so as to provide a thin surface or layer of titanium without compromising the flexibility of the structure. In a preferred mode, the titanium provides a surface layer of about 20-60 nm. Thicker layers may be employed depending on the flexibility of the polymeric material employed for the catheter and the level of flexibility required in use. As such the device remains flexible in order to be easily threaded through the body and through the serpentine like path through blood vessels, to place the distal end in the desired location.

However, it is still within the scope of the present invention to include a layer that is more than the preferred mode but still provides the flexibility as needed. This may be accomplished through employing a more flexible titanium or titanium alloy known in the art.

With respect to the above description, before explaining at least one preferred embodiment of the herein disclosed invention in detail, it is to be understood that the invention is not limited in its application to the details of construction and to the arrangement of the components in the following description or illustrated in the drawings. The invention herein described is capable of other embodiments and of being practiced and carried out in various ways which will be obvious to those skilled in the art. Also, it is to be understood that the phraseology and terminology employed herein are for the purpose of description and should not be regarded as limiting.

As such, those skilled in the art will appreciate that the conception upon which this disclosure is based may readily be utilized as a basis for designing of other structures, methods and systems for carrying out the several purposes of the present disclosed device. It is important, therefore, that the claims be regarded as including such equivalent construction and methodology insofar as they do not depart from the spirit and scope of the present invention.

It is an object of the invention to provide a bio-compatible catheter or PICC line, employable for prolonged periods in a patient.

It is a further object of the invention to provide a PICC line coated with a layer of titanium which does not require removal for either an MRI or an X-ray procedure.

It is still a further object of the invention to provide a titanium coated PICC line that maintains flexibility as needed for intravenous insertion.

BRIEF DESCRIPTION OF DRAWING FIGURES

DETAILED DESCRIPTION OF THE PREFERRED EMBODIMENTS OF THE INVENTION

Figure 1:
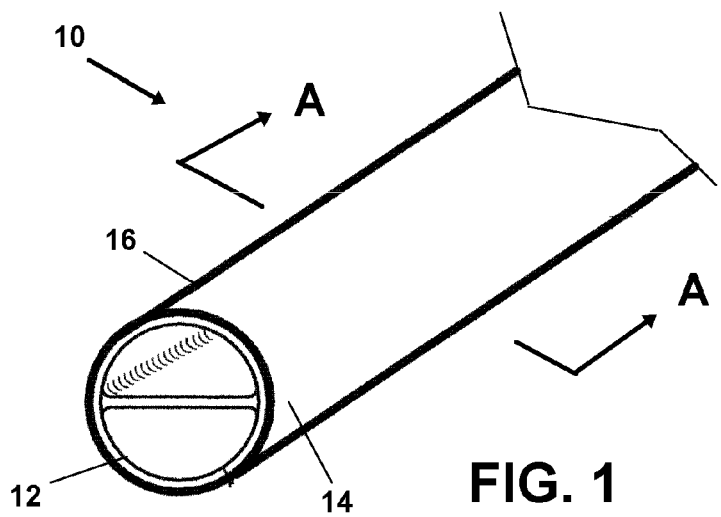
FIG. 1 shows an elevated view of the device depicting a multi lumen bearing component such as a catheter tube having a titanium surface.
Figure 2:
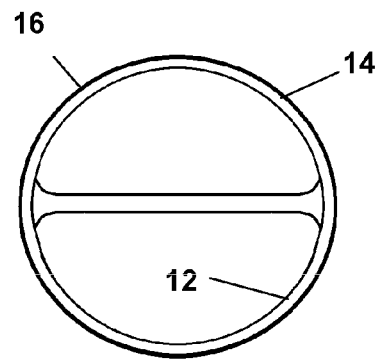
FIG. 2 is a cross section view of one mode of the device of FIG. 1, showing a catheter having two lumens, along cut line AA.

Now referring to drawings in FIGS. 1-7, wherein similar components are identified by like reference numerals, there is seen in FIG. 1 and FIG. 2 elevated and cross sectional views respectively of the device 10 comprising a catheter 12 having a layer of titanium 16 thereon which is coated or otherwise formed on the exterior surface area 14 of the catheter 12. The catheter 12 may be polyurethane or silicone or any other material known in the art for catheters and similar type tubing suited for receiving a titanium layer as is the intended scope of the device 10. Further, while shown as a double lumen catheter, those skilled in the art will realize that catheters come with varying numbers of internal lumens from one to multiples and the depicted dual lumen catheter 12 is for illustration purposes only since the invention herein is applicable to all catheters and tubes which may be employed in medical uses for insertion into a patient.

It is preferred that the catheter 12 maintains its flexibility as needed for intravenous insertion insofar as the titanium layer 16 is substantially thin and since titanium by nature is more ductile than other metals. In a particularly preferred mode the layer 16 on the exterior surface 14 of the catheter 12 is in the order of magnitude of 20-60 nm will perform well with titianium in a thickness depending on the flexibility of the formed polymeric catheter material, other thicknesses may be employed. In this manner, the catheter 12 employs the benefits of bio-compatibility and other benefits associated with the titanium layer 16 without compromising the flexibility of the structure needed for advancing the device 10 through the often serpentine like blood vessels to place the distal end in the desired location. Further, when wet, the titanium surface provides a means to overcome friction against the exterior of the catheter 12.

The titanium layer 16 is preferably formed by conventional methods such as coating, spraying, thermoforming, film engaging or other means known in the art. Further, it must be noted that in order to adhere or otherwise form the titanium layer 16 on some types of catheters 12 those skilled in the art may employ various other alloys of titanium better suited for varying types of tubing material and such is anticipated within the scope of this patent. Further, the polymeric material extruded as the catheter may be impregnated with titanium to a percentage allowing extrusion and yielding an exterior surface with a high percentage of titanium contacting body tissues.

Figure 3:
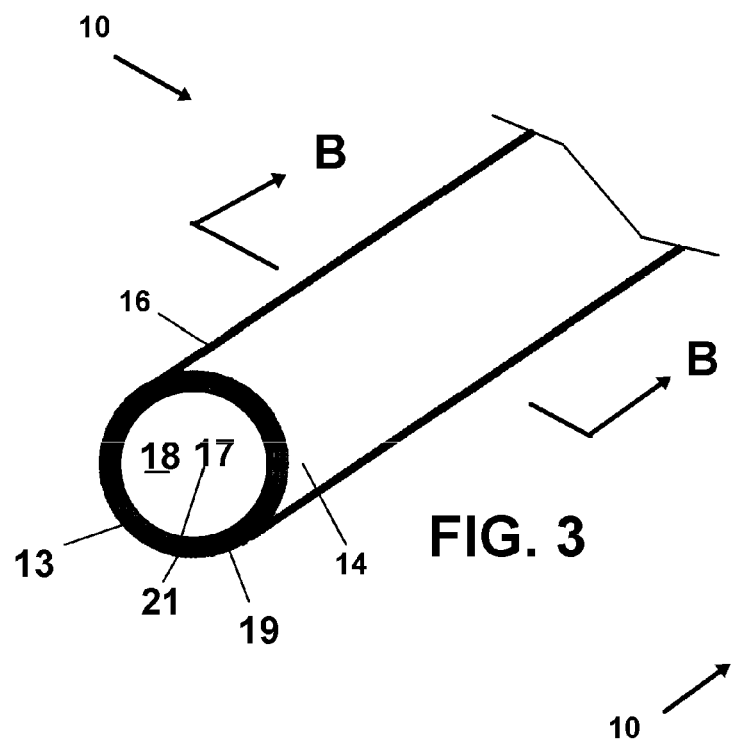
FIG. 3 shows an elevated view of the device depicting a single lumen catheter tube with the exterior surface, interior surface, and ends coated in titanium providing increased bio-compatibility.
Figure 4:
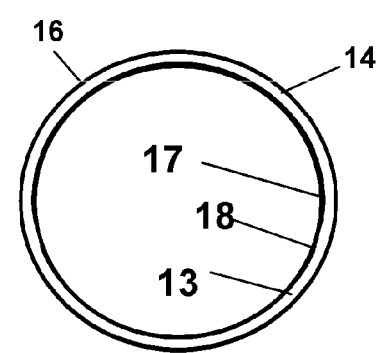
FIG. 4 is a cross section view of one mode of the device of FIG. 3, showing a single lumen catheter, along cut line BB of FIG. 3.

FIG. 3 and FIG. 4 show elevated and cross sectional views respectively of another preferred mode of the device 10 providing still increased bio-compatibility. Shown is a single lumen catheter 13 having a layer of titanium 17 on the interior surface 18 and a layer of titanium 19 on the end walls 21 in combination with a layer of titanium 16 on the exterior surface area 14 of the catheter 13. Again, the catheter 13 may be a polymeric material adapted to form a flexible conduit such as polyurethane or silicone or any other material known in the art for catheters and similar type tubing suited for receiving a titanium layer as is the intended scope of the device 10. By employing a surface of titanium on all surfaces, bio-compatibility, anti-pathogenic qualities, and increased lubricity are provided in all modes of employement of the device. Further, while shown as a single lumen catheter 13, the invention in this mode herein is applicable to all catheters and tubes which may be employed in medical uses for insertion into a patient and is not to be considered limited by the depiction.

Figure 5:
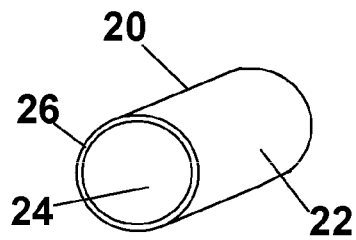
FIG. 5 shows an elevated view of another preferred mode of the device showing a catheter cuff coated in titanium.

Shown in FIG. 5 is a particularly preferred catheter cuff 20 shown having titanium coatings on the exterior surface 22, interior surface 24, and end walls 26. Such a cuff may be a tissue ingrowth stabilizing cuff or other cuff known in the art. As such, when the employment of such a cuff 20 is desired, the titanium coating assures bio-compatibility. It must be noted that it is also an object of the invention that other types of connectors, and ports, and other components employed in combination with a catheter, may similarly employ titanium on exposed exterior surfaces which may contact body tissue as needed for improved bio-compatibility, lubricity, and pathogen inhibitance. As such, all connectors and components which those skilled in the art would anticipate as being employed with the titaniam surfaced catheter herein, are considered to be capable of surfacing with the same titanium layer on exposed surfaces and considered within the scope of this disclosure.

Figure 6:
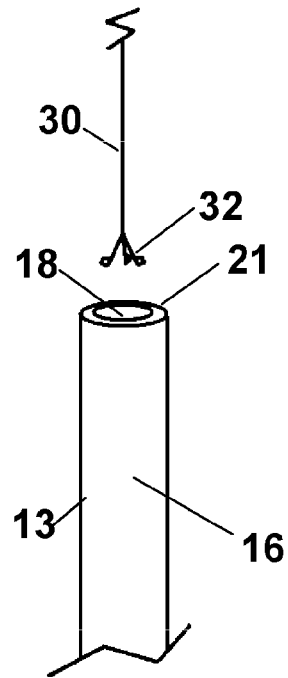
FIG. 6 is a view depicting a preferred method for applying a titanium coating to a lumen bearing device such as a catheter, plasma-activated chemical vapor deposition at a temperature lower than the melting point of the polymeric material of the catheter, showing the catheter disengaged from the mounting component.
Figure 7:
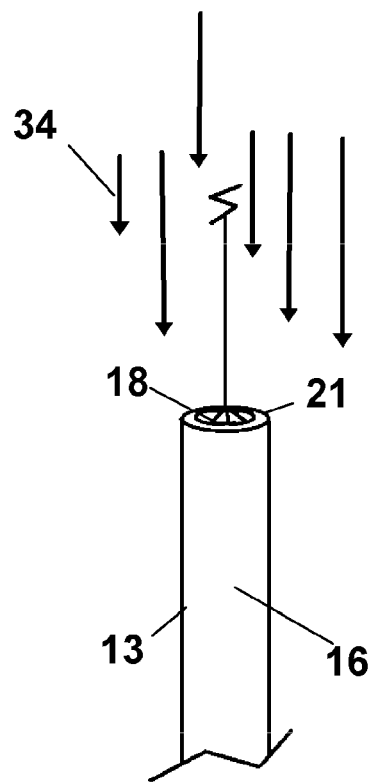
FIG. 7 shows a view of the method of FIG. 6 with the interior wall of the axial passage of the catheter is engaged to a mount and held vertical during the plasma-activated chemical vapor deposition process and a fan or air movement is employed to communicate the vapor through the axial chamber.

FIG. 6 and FIG. 7 show views of one preferred method for the plasma-activated chemical vapor deposition process employed for bonding titanium to the exterior surface 16, interior surface 18, and end walls 21 of a catheter 13 to form a titanium surface thereon bonded with the underlying polymeric surface such as silicone, polyethylene, or polyurethene. It must be noted that although a single lumen catheter 13 is depicted, the following method may be employed with any and all single and multi-lumen catheters employed in the medical and vetinary medical fields.

In all modes of the device herein, the titanium bonded surface is anticipated to be imparted at temperatures below the melting point of the underlyig lumen bearing device such as any type of catheter, to increase lubricity and biocompatibility thereof. The configuration of the titanium bonded into and on the exterior surface or surfaces of a catheter, to form a unitary structure layer, can be employed on any one or a plurality of such lumen bearing structures from a group including but not limited to Peritoneal Dialysis Catheters, Hemodialysis Catheters, Pleural and Peritoneal Drainage Catheters, Biliary Catheters, Ureteral Catheters, CV Catheters, Ventricular-Peritoneal Shunts, Ventricular Drainage Catheters, Ascites Shunts, Urinary Catheters, PICC lines, and any lumen bearing line which is inserted or implanted in a human or animal patient where the benefits of increased lubricity, anti-pathogenic qualities, and bio-compatibility are desirable.

Figure 7A:
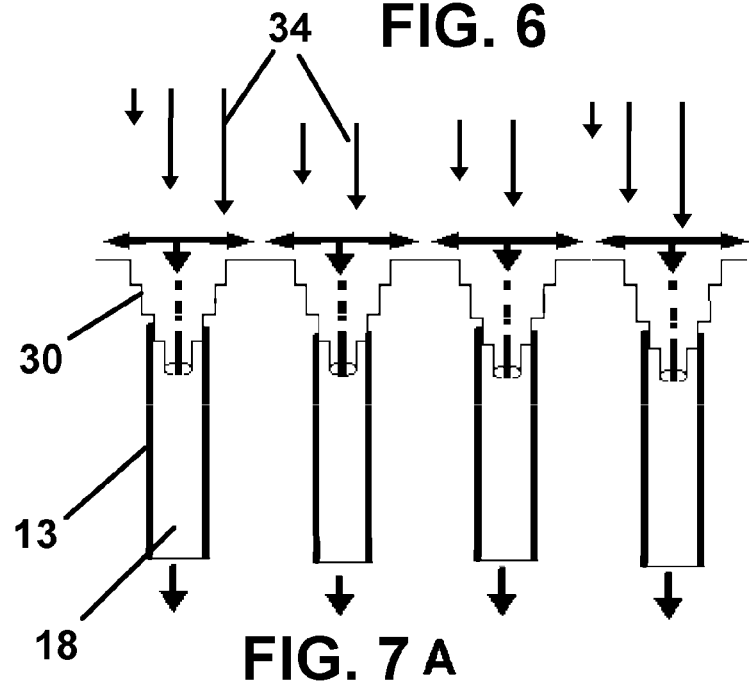
FIG. 7a depicts a slice through a plurality of catheters undergoing plasma-activated vapor deposition and showing the vapor induced to communicate through the lumen bearing device such as a catheter at temperatures below the melting point of the material forming the lumen, to impart titanium to the axial passage of the lumen or lumens.

As can be seen, in FIGS. 7 and 7a, a mount 30 having a plurality of engagement points such as prongs 32 at distal ends or steps in FIG. 7a, such that the catheter may be frictionally engaged with a passageway communicating into the axial passage at one end of a lumen in a catheter 13. The prongs 32 or steps are preferably shaped or otherwise formed to impart a slight outward biasing force on the interior surface 18 forming the lumen or lumens of the catheter 13 such as to frictionally and securely engage the catheter 13 as shown in FIGS. 7 and 7a.

During formation, with a lumen bearing device such as the depicted catheter 13 in this vertically disposed position, the gas 34 containing the titanium material is induced to flow through the axial passage by a fan or pump or other means to create the flow within the deposit chamber. The gas 34 is passed over the end of the catheter, the outside surface, and through the axial passage and inner surface, such that titanium material will be deposited on and bonded with the end walls 21, exterior surface 16, as well as pass through the interior surface 18 of the catheter 13, providing a coating thereon.

The present invention provides an improved bio-compatible catheter having a layer of titanium positioned on one or a combination of the interior surface, exterior surface, and endwalls.

While it is an object of the invention to provide a bio-compatible catheter tubing, with enhanced resistance to friction, and which need not be removed during an MRI and all of the fundamental characteristics and features of the invention have been shown and described herein, with reference to particular embodiments thereof, a latitude of modification, various changes and substitutions are intended in the foregoing disclosure and it will be apparent that in some instances, some features of the invention may be employed without a corresponding use of other features without departing from the scope of the invention as set forth. It should also be understood that various substitutions, modifications, and variations may be made by those skilled in the art without departing from the spirit or scope of the invention. Consequently, all such modifications and variations and substitutions are included within the scope of the invention as defined by the following claims.

What is claimed:

1. A lumen bearing component comprising:
   a lumen defined by an interior surface of a surrounding wall having an exterior surface and additionally having end wall surfaces communicating between said interior surface and said exterior surface, said lumen formed of polymeric material being flexible as needed for intravenous insertion and navigation;
   a titaniumized surface formed completely upon all of said exterior surface of said surrounding wall, said titaniumized surface also completely covering all of said interior surface; said titaniumized surface providing means for increased lubricity and bio-compatibility with a body of a patient in which said catheter is positioned;
   said titaniumized surface being the only surface formed completely on all of said exterior and said interior surface, and said titaniumized surface being composed exclusively of titanium; said titaniumized surface covering said exterior surface being covalent bonded with said exterior surface in a first layer having a thickness substantially being in a range between 20-60 nm; and
   maintaining said thickness within said range providing means to maintain a flexibility of the underlying polymeric material.

2. The lumen bearing component of claim 1 wherein said lumen bearing component is a catheter from a group of lumen bearing catheters including Peritoneal Dialysis Catheters, Hemodialysis Catheters, Pleural Drainage Catheters, Peritoneal Drainage Catheters, Biliary Catheters, Urethral Catheters, CV Catheters, Ventricular-Peritoneal Shunts, Ventricular Drainage Catheters, Ascites Shunts, Urinary Catheters, and PICC lines.

3. The lumen bearing component of claim 1, wherein the lumen bearing component is a catheter.

4. A lumen bearing component comprising:
   a lumen defined by an interior surface of a surrounding wall having an exterior surface and additionally having end wall surfaces communicating between said interior surface and said exterior surface, said lumen formed of polymeric material being flexible as needed for intravenous insertion and navigation;
   a titaniumized surface formed completely upon all of said exterior surface of said surrounding wall, said titaniumized surface completely covering all of said interior surface, said titaniumized surface being the only surface formed completely on all of said exterior and said interior surface;
   said titaniumized surface being composed exclusively of titanium, said titaniumized surface providing means for increased lubricity and bio-compatibility with a body of a patient in which said catheter is positioned; said titaniumized surface covering said exterior surface is covalent bonded with said exterior surface in a first layer, said first layer having a thickness substantially being in a range between 20-60 nm; and
   maintaining said thickness within said range providing means to maintain a flexibility of the underlying polymeric material.

5. The lumen bearing component of claim 4 wherein said lumen bearing component is a catheter from a group of lumen bearing catheters including Peritoneal Dialysis Catheters, Hemodialysis Catheters, Pleural Drainage Catheters, Peritoneal Drainage Catheters, Biliary Catheters, Ureteral Catheters, CV Catheters, Ventricular-Peritoneal Shunts, Ventricular Drainage Catheters, Ascites Shunts, Urinary Catheters, and PICC lines.

6. The lumen bearing component of claim 4, wherein the lumen bearing component is a catheter.

7. A lumen bearing component comprising;

a lumen defined by an interior surface of a surrounding wall having an exterior surface and additionally having end wall surfaces communicating between said interior surface and said exterior surface, said lumen formed of polymeric material being flexible as needed for intravenous insertion and navigation; and a titaniumized surface formed completely upon all of said exterior surface of said surrounding wall, said titaniumized surface also completely covering all of said interior surface, said titaniumized surface also completely covering all of said end wall surfaces, said titaniumized surface providing means for increased lubricity and bio-compatibility with a body of a patient in which said catheter is positioned, said titaniumized surface being the only surface formed completely on all of said exterior and said interior surface, and said titaniumized surface being composed exclusively of titanium;

wherein said titaniumized surface covering said exterior surface is covalent bonded with said exterior surface, said interior surface and said end surfaces in a first layer, said first layer having a thickness substantially being in a range between 20-60 nm.

* * * * *